(12) United States Patent
Hsu et al.

(10) Patent No.: US 6,468,285 B1
(45) Date of Patent: Oct. 22, 2002

(54) SURGICAL INSTRUMENTS AND PROCEDURES

(75) Inventors: Thomas H. S. Hsu, Cleveland Heights; Inderbir S Gill, Beachwood; Mark S. Goodin, Solon; Bryan P. Byermann, South Euclid; Helmuth Kotschi, Cleveland, all of OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/389,724

(22) Filed: Sep. 3, 1999

Related U.S. Application Data
(60) Provisional application No. 60/099,107, filed on Sep. 3, 1998.

(51) Int. Cl.[7] .............................................. A61B 17/08
(52) U.S. Cl. ...................................................... 606/158
(58) Field of Search ............................... 606/151, 205, 606/152, 153, 157, 158, 142, 143, 144, 145, 147, 148, 150; 81/7, 303, 312, 3.8

(56) References Cited

U.S. PATENT DOCUMENTS

| | | | | |
|---|---|---|---|---|
| 1,170,334 A | * | 2/1916 | Riggs ........................... | 606/158 |
| 3,316,914 A | * | 5/1967 | Collito ......................... | 606/158 |
| 4,245,638 A | * | 1/1981 | Lebeck et al. ............... | 606/158 |
| 4,316,470 A | * | 2/1982 | Braun et al. ................. | 606/158 |
| 4,630,608 A | * | 12/1986 | Arroyo ......................... | 606/158 |
| 4,635,636 A | * | 1/1987 | Goldstein .................... | 606/158 |
| 4,635,638 A | * | 1/1987 | Weintraub et al. ........... | 606/147 |
| 4,681,109 A | * | 7/1987 | Arroyo ......................... | 606/158 |
| 5,011,487 A | * | 4/1991 | Shichman .................... | 606/158 |

\* cited by examiner

*Primary Examiner*—Henry J. Recla
*Assistant Examiner*—Tan-Uyen T. Ho
(74) *Attorney, Agent, or Firm*—Calfee, Halter & Griswold LLP

(57) ABSTRACT

Paired vascular clamps simplify laparoscopic vascular reconstruction surgery by providing an instrument for bringing vessel ends together to a reasonable working distance under a controlled fashion. A first clamp, with a pivoted connecting arm, and a second clamp with a lock/release device for attaching the second clamp to the connecting arm, can be inserted through an trocar or other port into a surgical field and then positioned on with the first clam and the second clamp in side-by-side and substantially parallel relationship, so that said first clamp and said second clamp can hold and position one or more vessels or elongated tissues. A laparoscopic approximator-everter has extendable blades for gripping blood vessel edges or other tissue to be anamosted, and an extendable sheath that can be advanced to surround the blades. Notches in the end of the sheath automatically evert and approximate the blood vessel edges for laparoscopic clip application or suturing when the sheath is advanced to surround the blades.

14 Claims, 16 Drawing Sheets

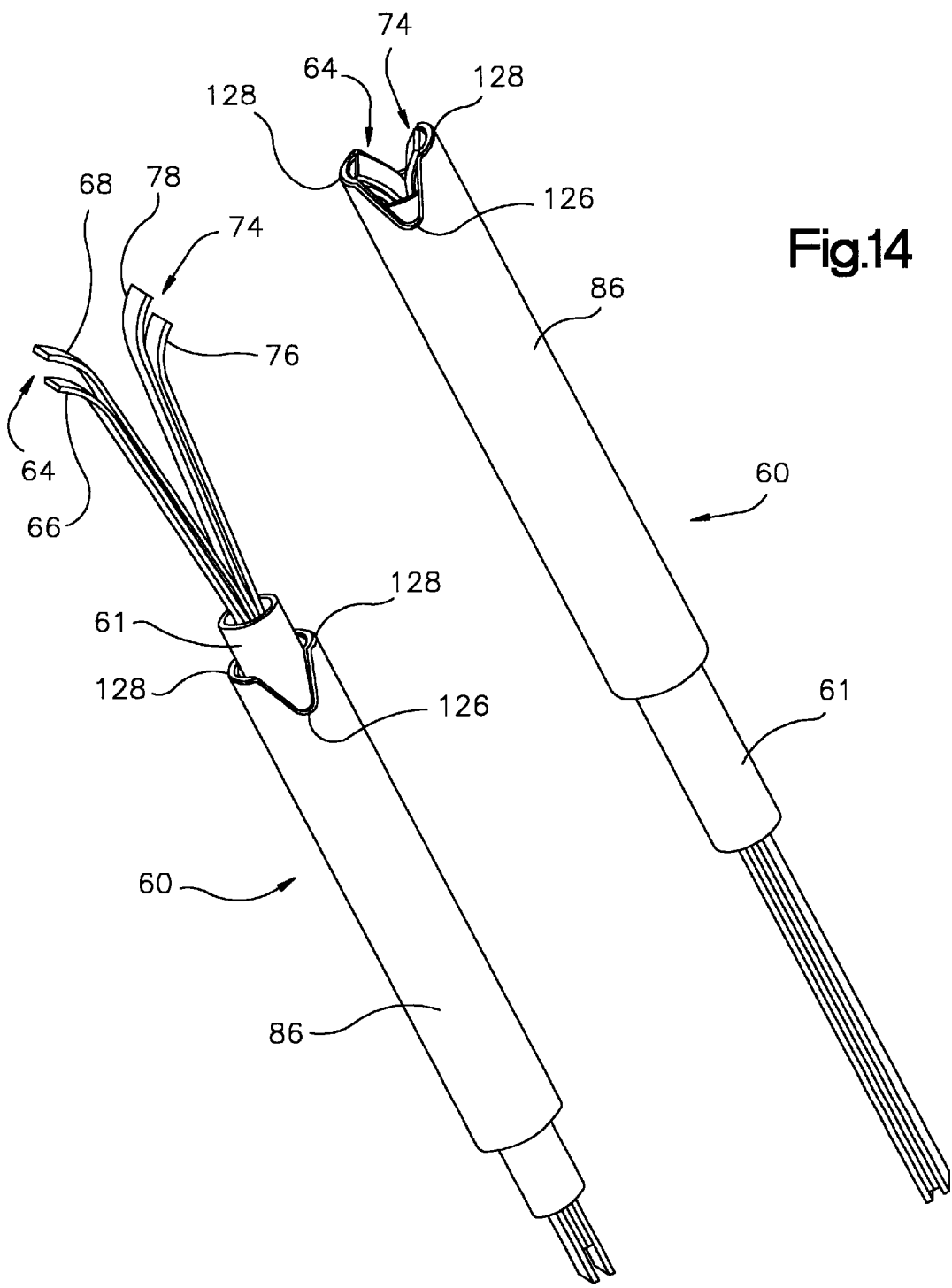

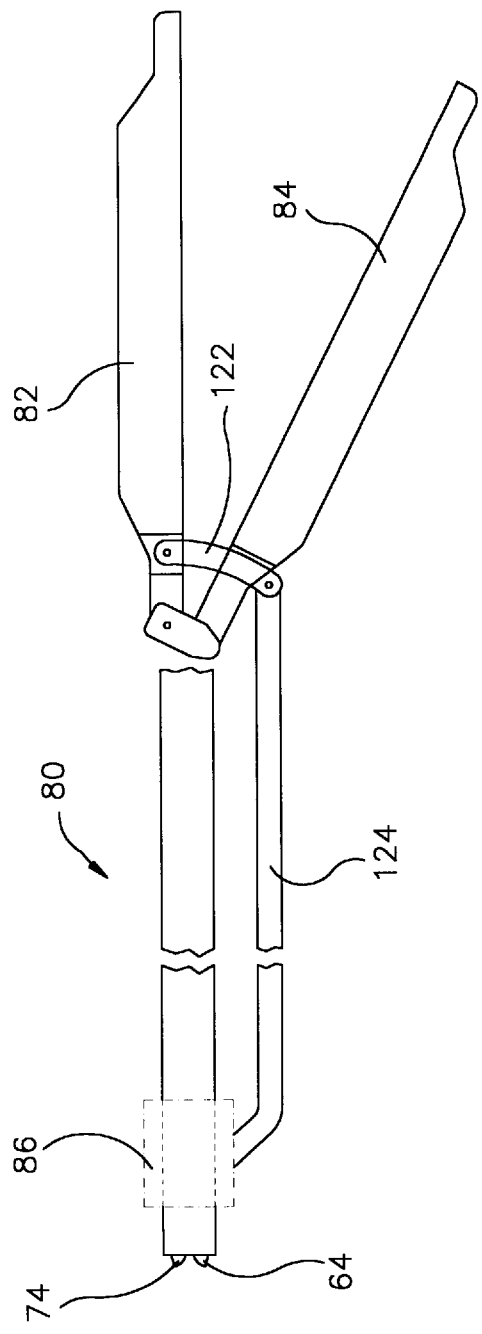
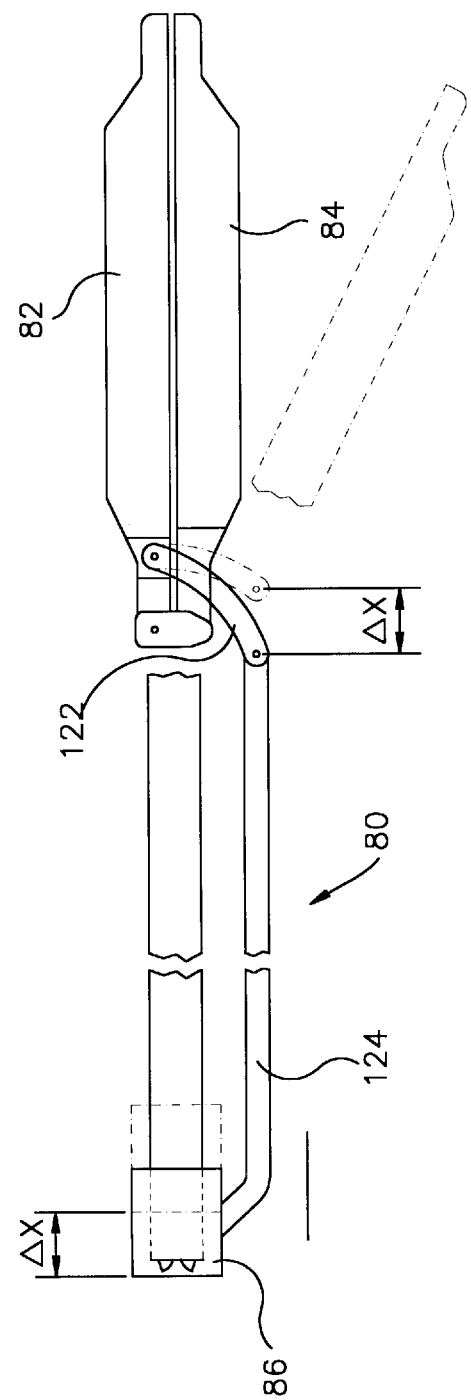

SURGICAL INSTRUMENTS AND PROCEDURES

CROSS-REFERENCE TO RELATED APPLICATIONS

This application claims the benefit of United States priority under 35 USC§119(e) of our copending U.S. provisional application Ser. No. 60/099,107, filed Sep. 3, 1999.

FIELD OF THE INVENTION

The present invention pertains generally to surgical instruments and procedures. More particularly, the invention relates to instruments and procedures that are specifically designed for laparoscopic vascular surgery, but have important applications in other surgical procedures.

BACKGROUND

Vascular surgery has traditionally been performed by making an open incision, or incisions, in the patient large enough for the surgical team to gain access and perform the procedure with hand instruments. These conventional open vascular bypass procedures are well known for their significant post-operative morbidity and recovery time and may be unavailable to certain patients of advanced age or preexisting medical conditions.

Laparoscopic (or endoscopic, thoracoscopic, etc., hereinafter collectively referred to as "laparoscopic") surgical methods, first introduced in 1991 when Schuessler et al reported the initial results of pelvic lymphadenectomy (W. W. Schuessler, T. G. Vancaillie, H. Reich and D. P. Griffith, Transperitoneal Endosurgical Lymphadenectomy in Patients with Localized Prostate Cancer, J. Urol 1991:145:988–991), have gained an increasingly important role in modern surgery. Tremendous advances have been made and laparoscopic technology, in which access to the abdominal cavity and its enclosed anatomy is by small trocars or ports in the abdominal wall, has been applied to many abdominal and pelvic urological procedures (I. S. Gill, R. V. Clayman and E. M. McDougall, Advances in Urological Laparoscopy, J. Urol 1995:154:1275–1294). Laparascopy is far less invasive, which reduces postoperative morbidity, recovery periods, hospital stays, healthcare costs and unsightly scars. However, the role of laparoscopy in vascular surgery has been virtually nonexistent.

In 1993 Dion et al reported the first laparoscopic vascular procedure—a laparoscopically assisted aorto-bifemoral bypass procedure (Y. M. Dion, N. Katkhouda, C. Rouleau and A. Aucoin, Laparoscopic-assisted Aortobifemoral Bypass, Surg. Laparosc Endosc. 1993:5:425–429). In this report, laparoscopy was only used to perform dissection and mobilization of the vessels, after which minilaparotomy and conventional hand-sewn vascular anastomoses were performed. Since then, only a handful of laparoscopic vascular procedures have been reported. In these cases, again, a minilaparotomy was often made, and vascular anastomosis was performed using conventional surgical techniques and instruments. Up to this time, we are only aware of one report of laparoscopic vascular anastomosis (S. S. Ahn, M. F. Clem, B. D. Braithwaite et al, Laparoscopic Aortofemoral Bypass —Initial Experience in an Animal Model, Annals of Surgery (1995) Vol. 222, No. 5, at 677–683) which reports an aortofemoral artery bypass performed with needle suturing in a porcine model. Other laparoscopic vascular surgical techniques are described in: Laparoscopic-assisted Abdominal Aortic Aneurysm Repair, Surgical Endoscopy (1995) 9:905–907; Laparoscopic vascular surgery: Four case reports, Journal of Vascular Surgery (1995) Vol. 22, No. 1, pages 73–79; Endovascular repair of two abdominal aortic aneurysms, Journal of Vascular Surgery (August 1995) Vol. 22, No. 2, pages 201–202; Video-assisted, Retroperitoneal Approach for Abdominal Aortic Aneurysm Exclusion, The American Journal of Surgery, Vol. 172 (October 1996), pages 363–365; Experimental Laparoscopic Aortic Aneurysm Resection and Aortobifemoral Bypass, Surgical Laparoscopy & Endoscopy, Vol. 6, No. 3, pp. 184–190; and in U.S. Pat. Nos. 5,211,683; 5,304,220; 5,330,490; 5,452,733 and 5,634,941.

Many difficulties with and drawbacks of current techniques for vascular surgery are attributable to the properties of blood vessels. Their walls are elastic, and the two ends of a transected vessel retract in opposite directions. The distance between the retracted vessel ends frequently becomes too great for anamostosis. Thus, there is a need for instruments and procedures with which the surgeon can approximate the vessel ends, i.e. bring them close to each other and align them properly for surgery.

Eversion of the edges of blood vessels prior to suturing, vessel clipping or other reconstructive surgical procedures to achieve intima-intima approximation is critical to a successful clinical outcome. This, in fact, is a fundamental step in all types of vascular anastomotic procedures, including all types of conventional open surgeries. Failure to achieve intima-intima approximation by eversion may result in anastomotic site narrowing, stricture formation, aneurysms and other undesirable surgical sequelae. In open surgeries, eversion may be performed with vascular forceps, but forceps which will perform this function effectively in laparoscopic surgery do not exist. There is, in fact, no laparoscopic instrument that will effectively and reliably evert vessel or tissue edges. The lack of instruments that will perform this function effectively and reliably is a major obstacle to the development of laparoscopic vascular surgery.

SUMMARY OF THE INVENTION

The paired vascular clamps disclosed herein greatly simplify laparoscopic vascular reconstruction surgery by providing an instrument for bringing vessel ends together to a reasonable working distance under a controlled fashion. The size of the clamps can be varied to suit various procedures, and the clamps can be preassembled before insertion or assembled intracorporeally, either before or after attachment to vessels to be anastomosed. Thus, these clamps provide an effective, flexible and reliable instrument which the laparoscopic surgeon can use in the reconnection of severed blood vessels, the repair or reconstruction of vessels or other tissue or other laparoscopic surgical procedures, such as ureteral reconstruction in urologic surgery and fallopian tube reconstruction in gynecologic surgery. Other applications include orthopedic procedures such as tendon and ligament repair. Surgeons who perform reconstruction of any tubular or other elongated tissue may benefit from this device.

This invention also provides a laparoscopic approximator-everter that approximates and everts two blood vessel edges for laparoscopic clip application or suturing with precision and ease. The same instrument can be used to approximate and evert other tissue edges to facilitate other forms of laparoscopic suturing in other types of surgery such as urologic surgery, gynecology, cardiovascular surgery, general surgery and the like. The instrument can be used with tubular structures such as blood vessels and the like, and with non-tubular tissues. Like the paired vascular clamps, this approximate-everter is an effective, flexible and reliable instrument for the laparoscopic surgeon.

DRAWINGS

FIGS. 1 and 2 are enlarged perspective views of paired vascular clamps specially adapted for this invention. One clamp bears a connecting arm that links the clamps. The other bears a lock/release control.

FIG. 8 is partially cut away and FIG. 9 is both cut away and further enlarged to show details that facilitate proper connection, alignment and adjustment of the paired clamps.

FIGS. 11 and 12 are partially cut away, and FIG. 12 is further enlarged, to illustrate the connection between the clamps via the connecting arm and lock/release control.

FIG. 13 is a perspective view of an approximator-everter in the open position.

FIG. 14 is a perspective view of the same approximator-everter in the closed position.

FIGS. 19a, and 19b are side elevation views, in the open and actuated positions, of an actuating mechanism for the approximator-everter in FIGS. 13–18.

Figure 20:
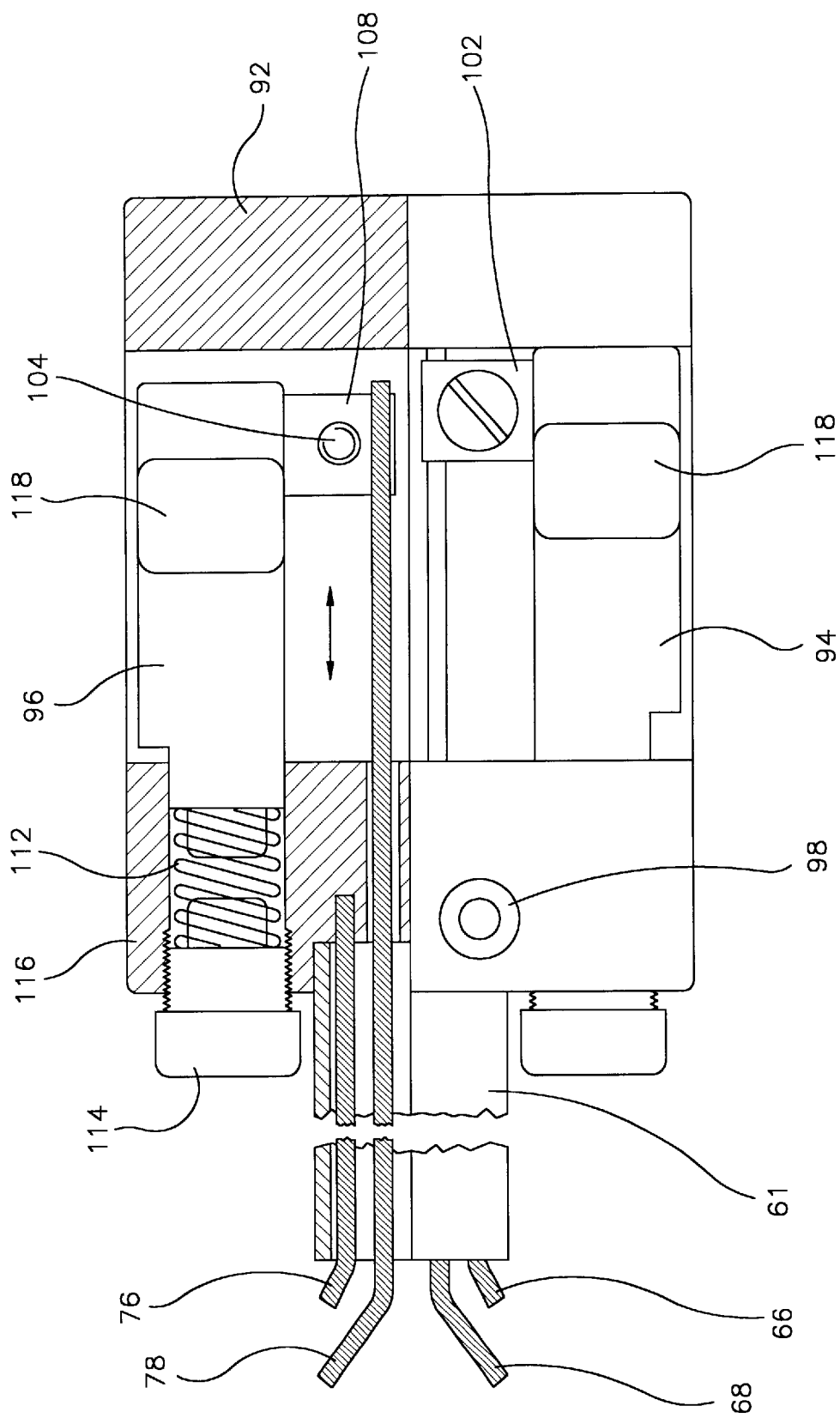

FIG. 20 is a partly cross-sectioned, fragmentary top plan view of the actuating mechanism shown in FIGS. 19a and 19b.

Figure 21:
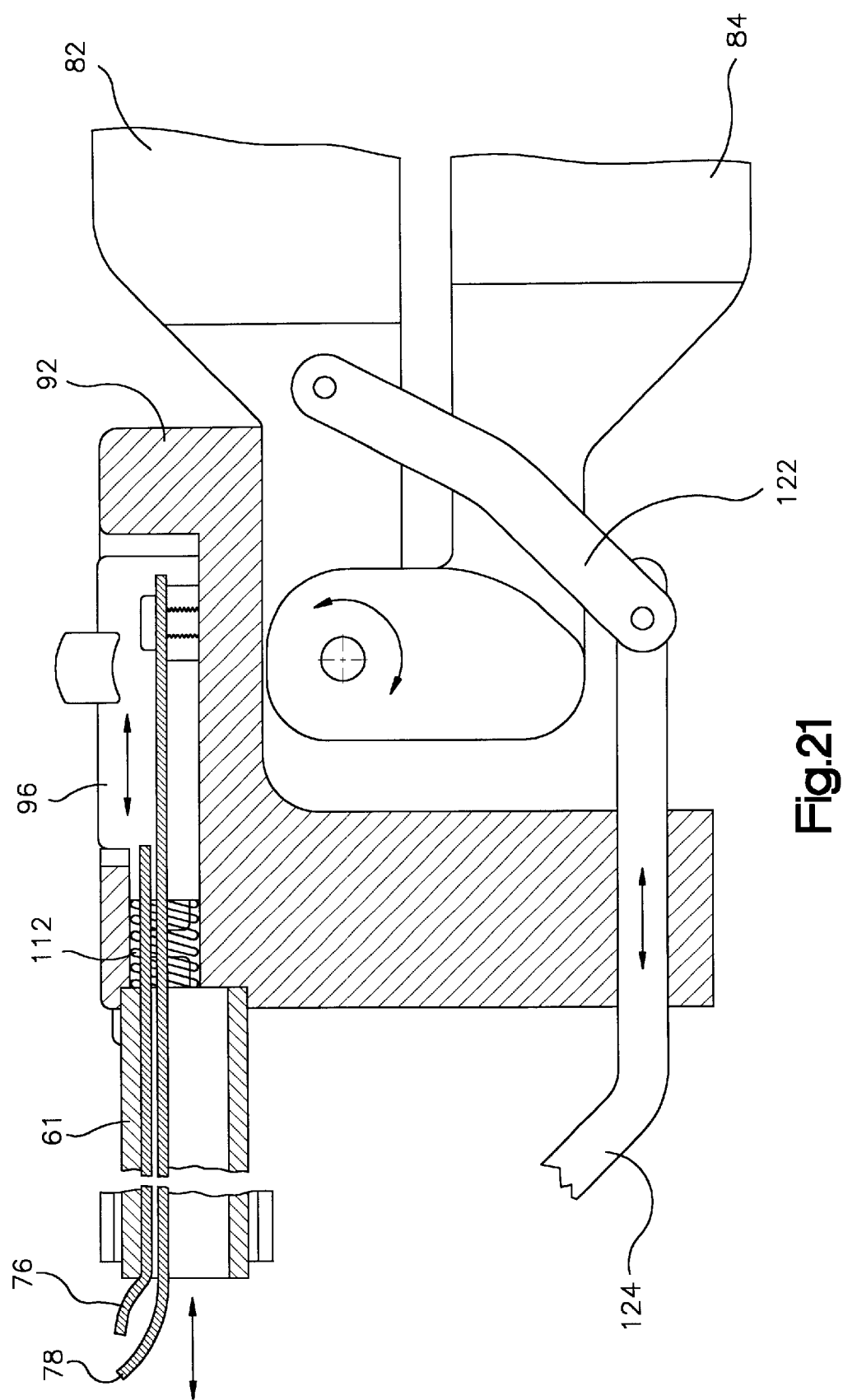

FIG. 21 is a partly cross-sectioned, fragmentary side elevation view, from the same vantage point as FIGS. 19a and 19b, of the actuating mechanism shown in those FIGS.

Figure 22:
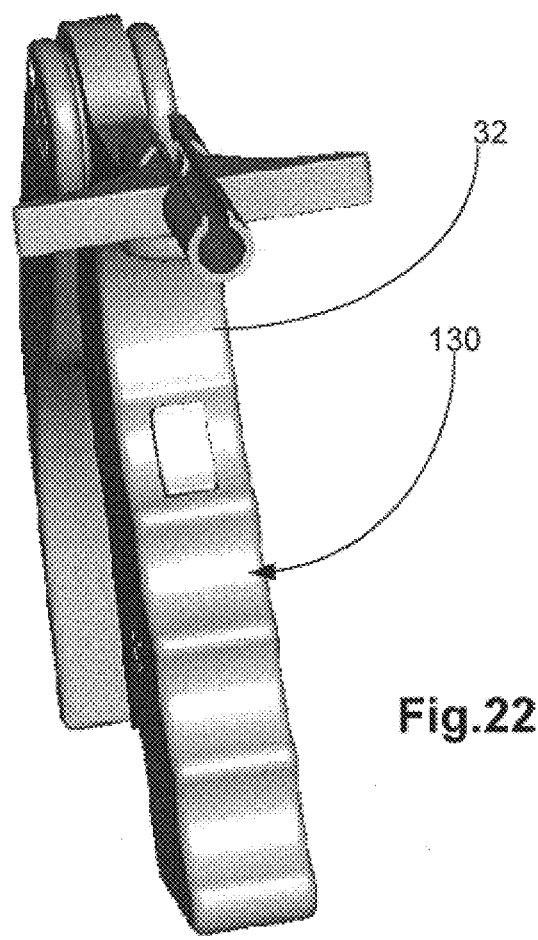
Figure 23:
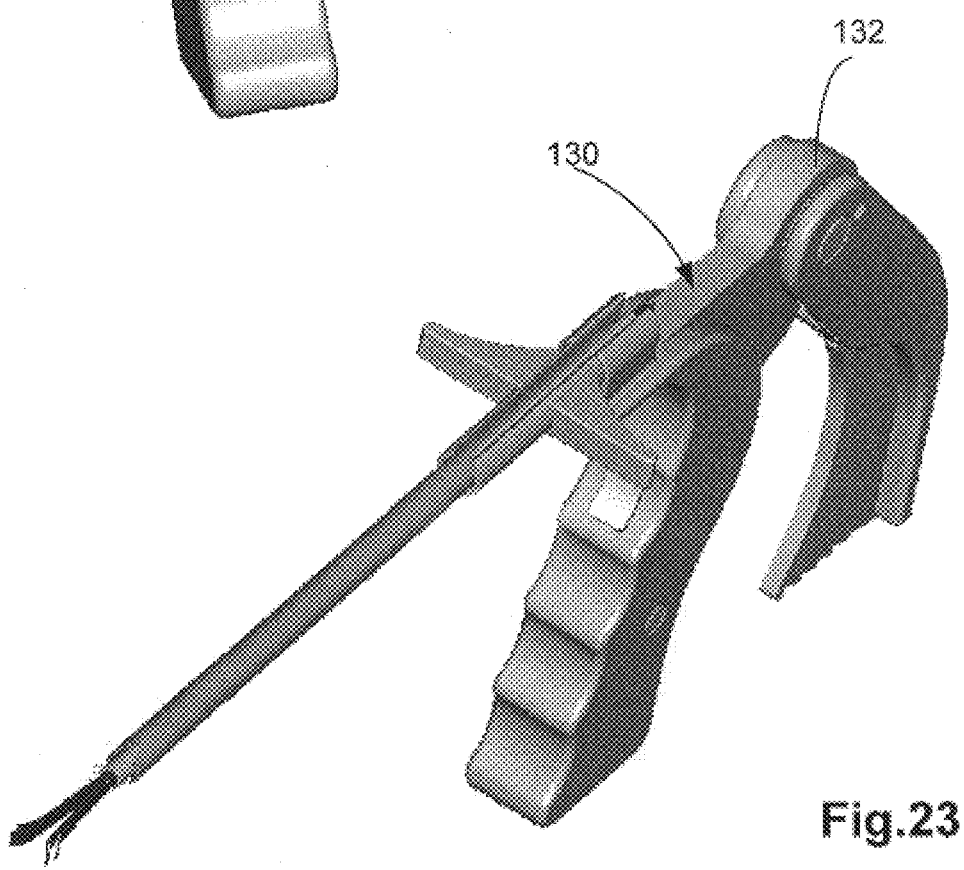

FIGS. 22 and 23 are perspective views of another actuating mechanism for the illustrated approximator-everter.

Figure 24:
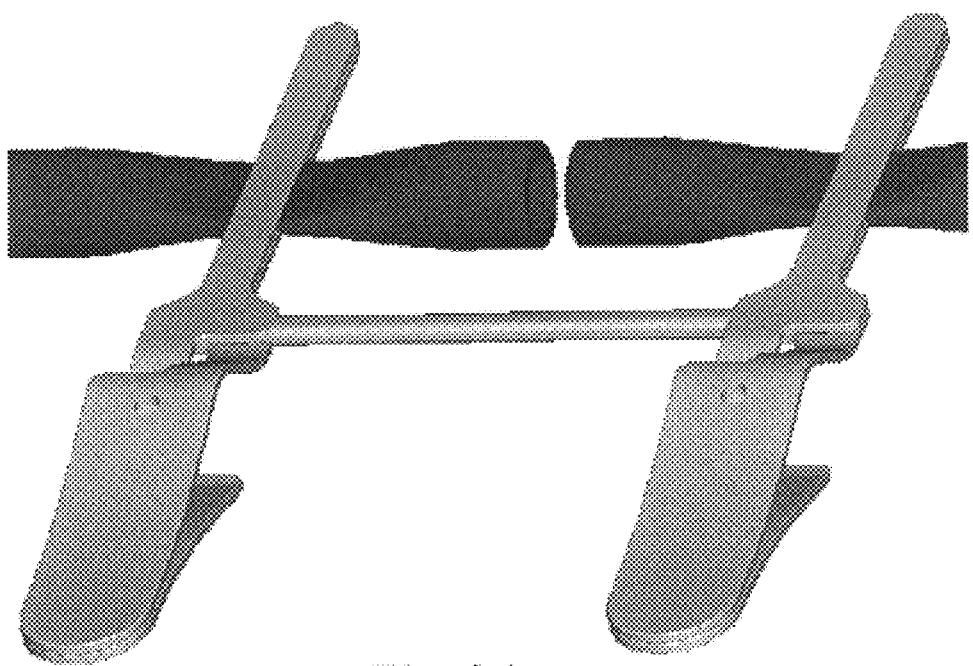
Figure 25:
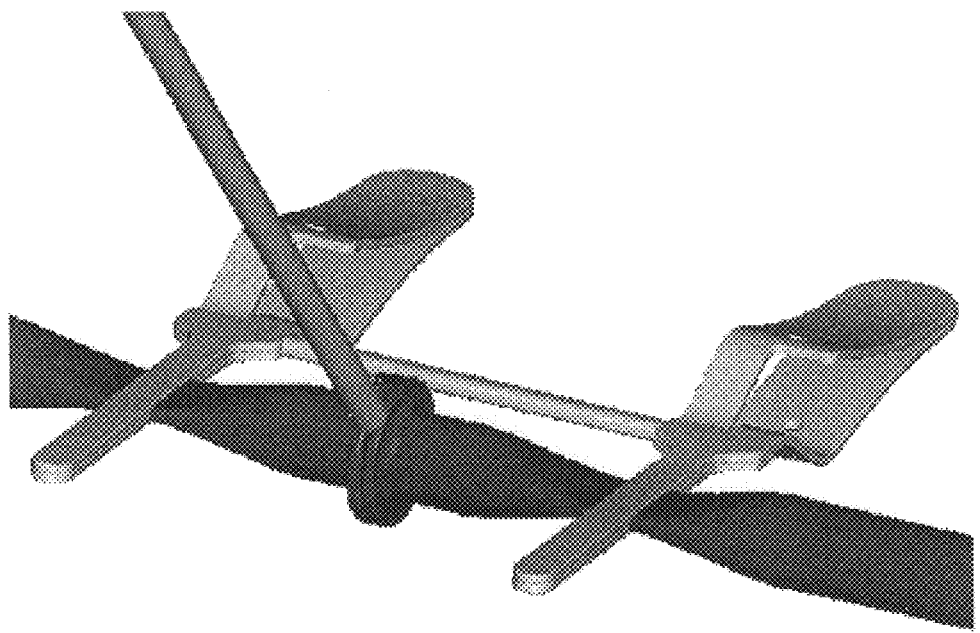

FIGS. 24 and 25 are schematic representations of the approximation, eversion and anastomosis of a simulated blood vessel with the instruments and procedures of this invention.

Figure 26:
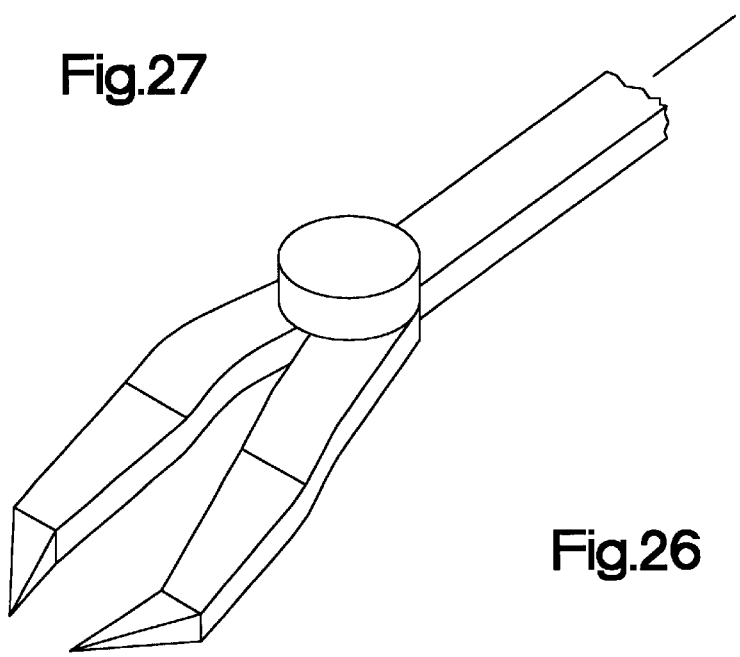

FIG. 26 is a perspective view of novel laparoscopic vascular forceps.

Figure 27:
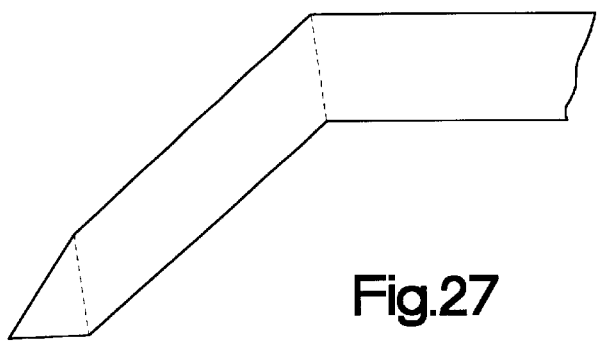

FIG. 27 is a side view of the forceps in FIG. 23.

Figure 28A:
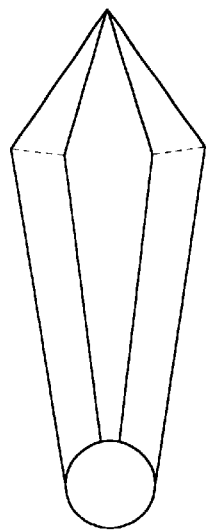
Figure 28B:
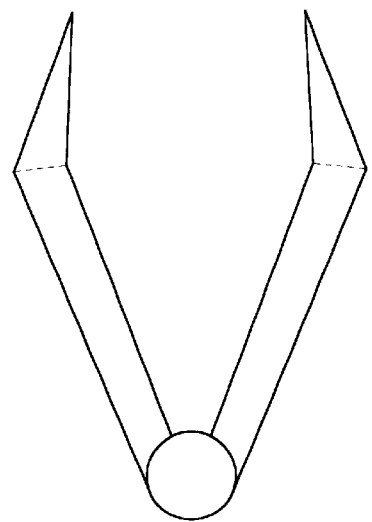

FIGS. 28(a) and 28(b) are top plan views of the forceps in the closed and open position.

Figure 29:
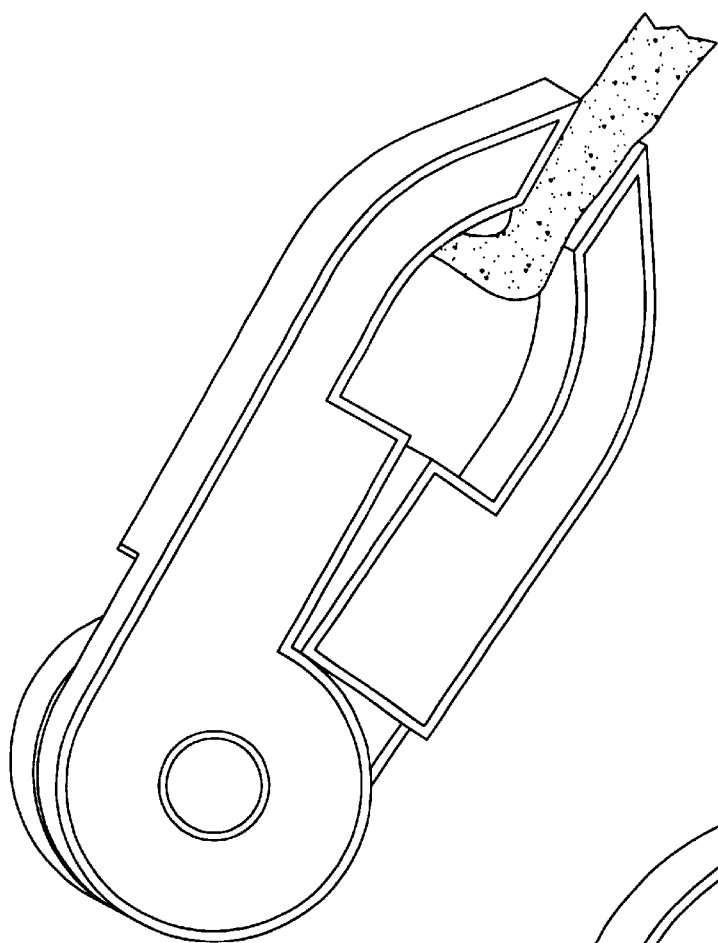

FIG. 29 is a perspective view of another embodiment of the jaws for the forceps, with the forceps gripping a piece of tissue in the distal clamp.

Figure 30:
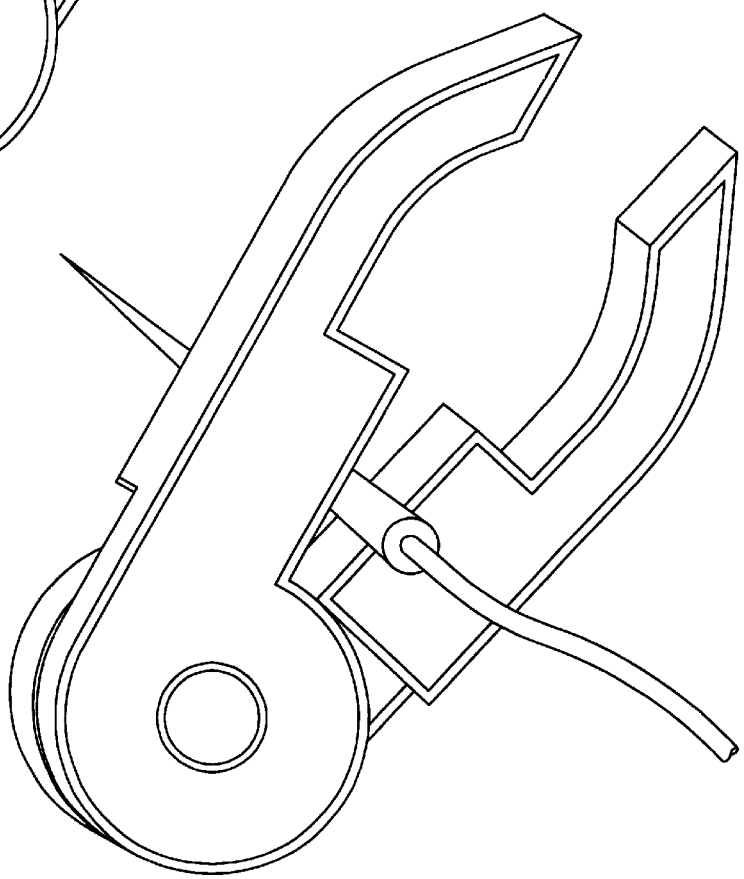

FIG. 30 is a perspective view of the jaws shown in FIG. 29, showing the use of the forceps to hold a needle in a proximal clamp.

DETAILED DESCRIPTION

Figure 1:
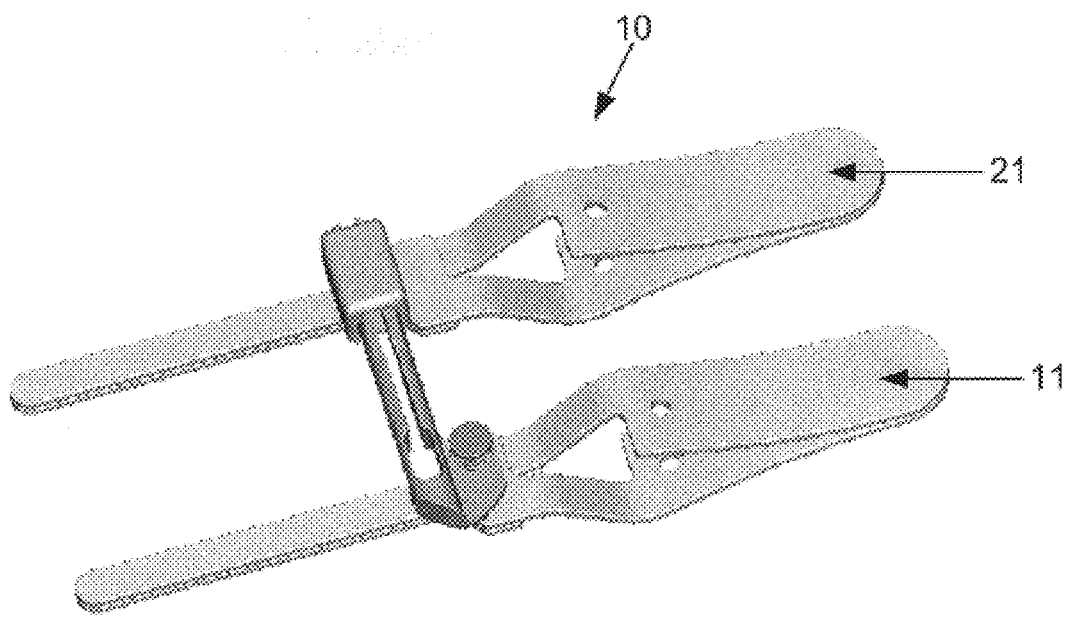

The paired vascular clamps illustrated in FIGS. 1 and 9–11, referred to generally as 10, are modified versions of conventional vascular bulldog clamps. (The illustrated clamps are commercially available from Instrumentarium, Teneboonne, Quebec, Canada, but other conventional clamps can also be used.) When fully assembled, the individual clamps 11, 21 are normally positioned side-by-side, substantially oriented in the same plane, and substantially parallel, as illustrated in FIG. 1. The individual clamps shown in FIGS. 2–5 and 6–8 can be inserted into the surgical field through conventional trocars or other ports and applied (using commercially available clamp applicators) to occlude vessel lumens. The size of the clamps, and the trocars through which they are inserted, may be varied to suit the size of the blood vessels or other tissues to be anastomosed.

The clamps can be assembled intracorporeally (with conventional laparoscopic clamp applicators, forceps or the like) to place the vessel ends in close juxtaposition in preparation for anastomosis, and to hold the ends of the vessel to be joined in the desired approximate position for suturing, clamp application or the like. It is normally preferable, particularly where the vessels to be anastomosed are not aligned, or have retracted a substantial distance apart, to apply the individual clamps to the ends of the two vessels to be joined and then join the two clamps together. Similarly, if the clamps are to be applied to an individual vessel from which a damaged, diseased or otherwise defective section will be removed, the separated clamps will normally be applied on either side of the defective section, and connected after the section has been removed. However, if the vessels are adequately aligned (normally in a straight line) and relatively close together, it may be preferable to join the two clamps together and then apply the clamps to the vessel ends. The distance between the clamps can then be adjusted as described below to complete the approximation of the vessels.

The first clamp 11, shown in FIGS. 3–6, has a specially designed connecting arm 12 that extends between and connects the two clamps in the assembled position illustrated in FIG. 1. Connecting arm 12, which in the preferred embodiment is mounted on a pivot 14 and biased by a coil spring 16 into the lateral position shown in FIGS. 1 and 6, in which the connecting arm is substantially perpendicular to the axis of the first clamp 11, pivots to extend axially along the jaws 19 of the clamp when the clamp is passed through the trocar or other port into the surgical field. Arm 12 automatically pivots back into the lateral position shown in FIGS. 1 and 6 (perpendicular to the axis of the clamp) when the clamp has passed through the trocar into the body cavity. When this clamp is retrieved at the end of the surgical procedure, the clamp is again turned so that the actuating end of the clamp (opposite jaws 19) enters the trocar first, and the connecting arm automatically pivots into an axial position along the jaws, which pass through the trocar last as the clamp is withdrawn.

Figure 2:
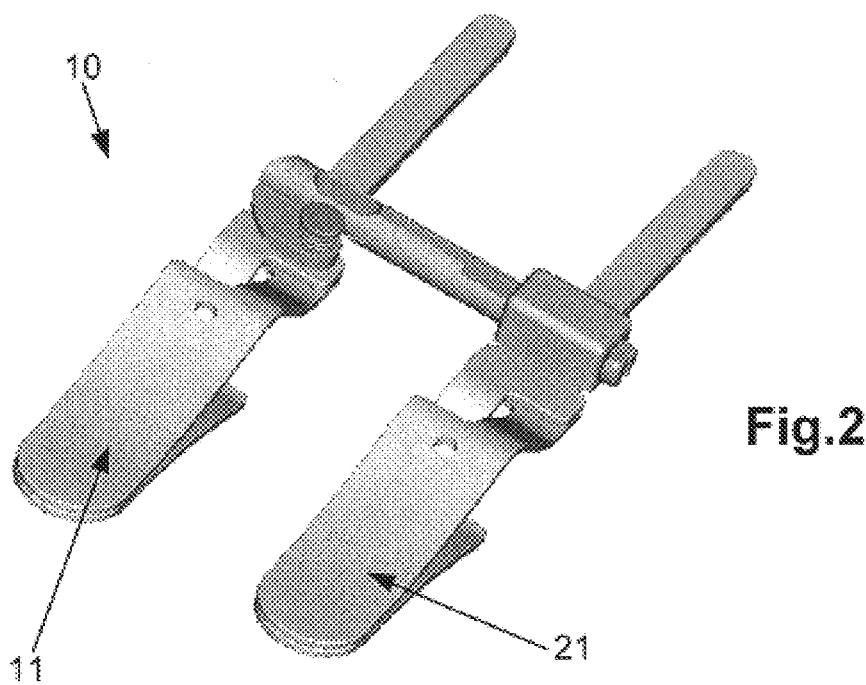
Figure 6:
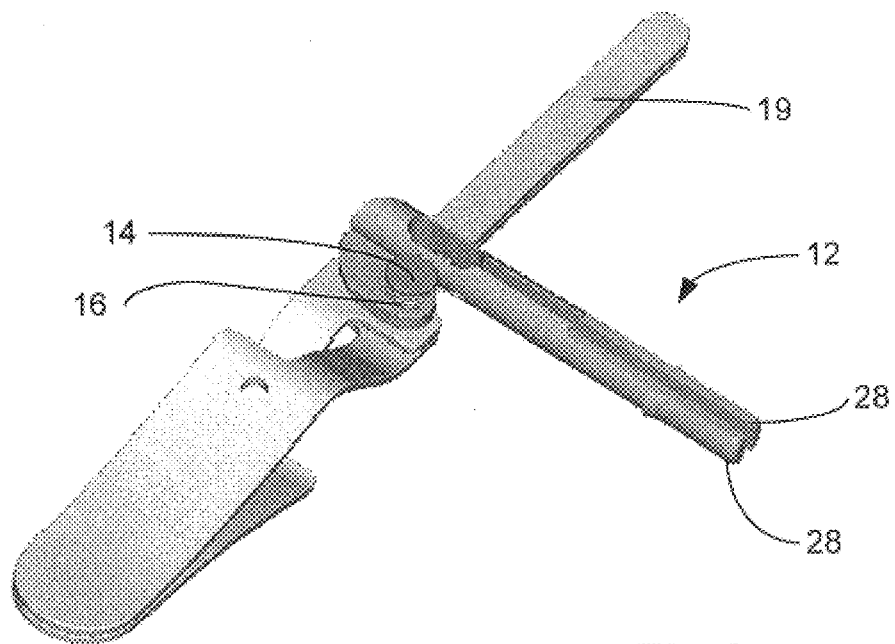
Figure 7:
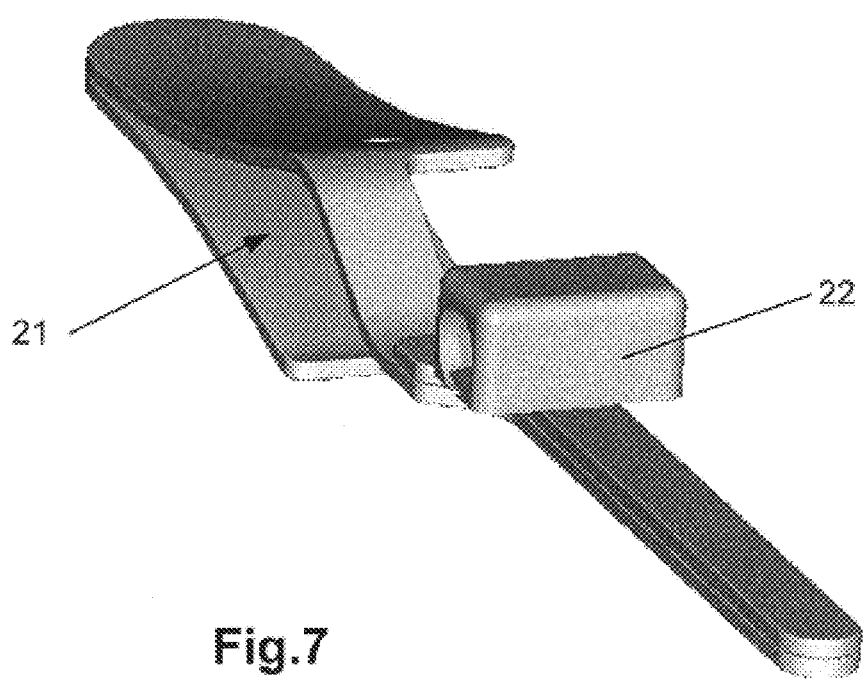
FIGS. 7–9 are perspective views of the clamp that bears the lock/release control.
Figure 8:
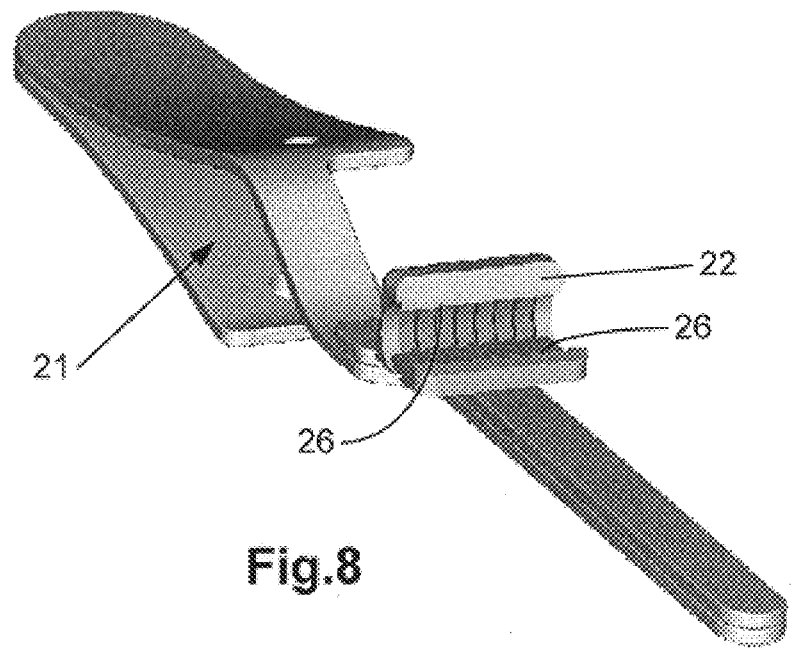
Figure 9:
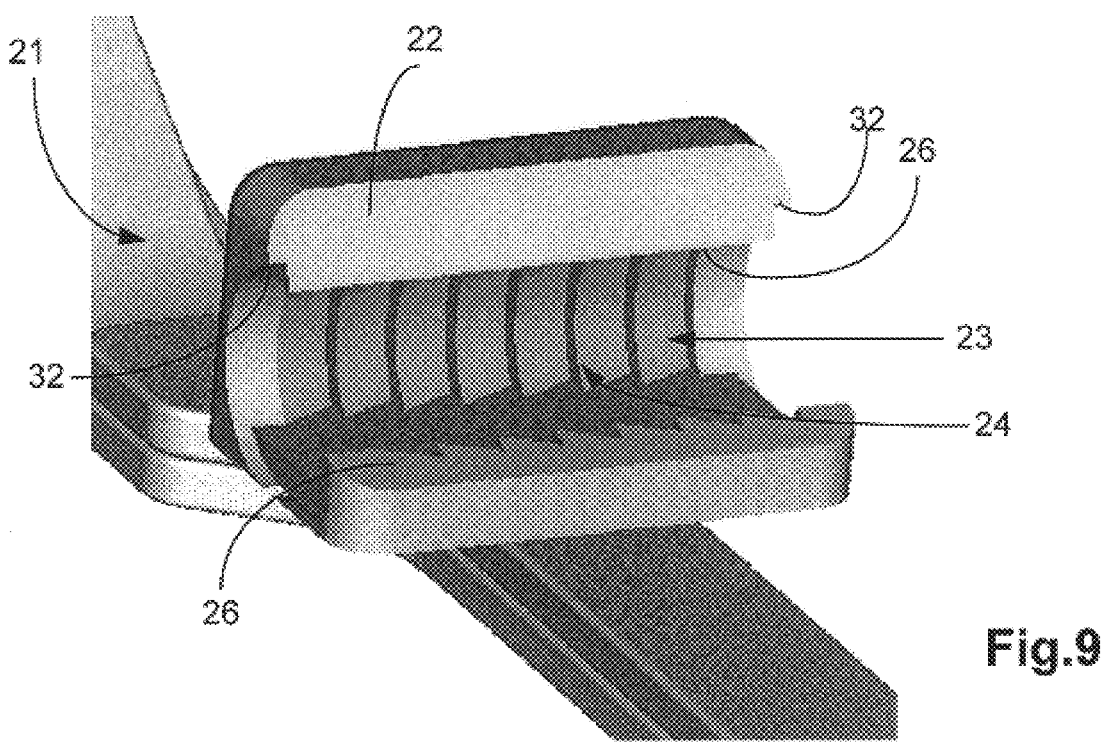
Figure 10:
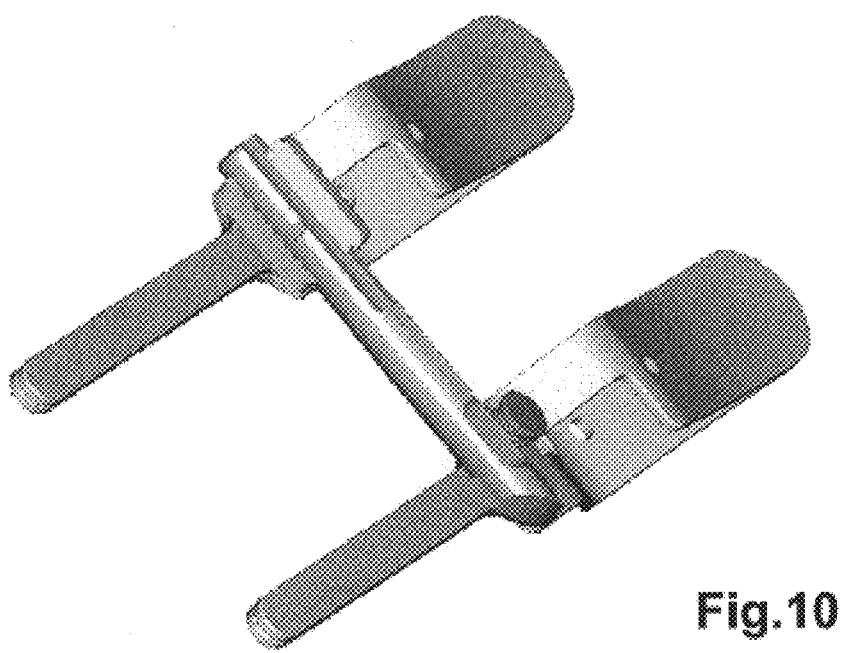
FIGS. 10–12 are further perspective views of the paired clamps.
Figure 11:
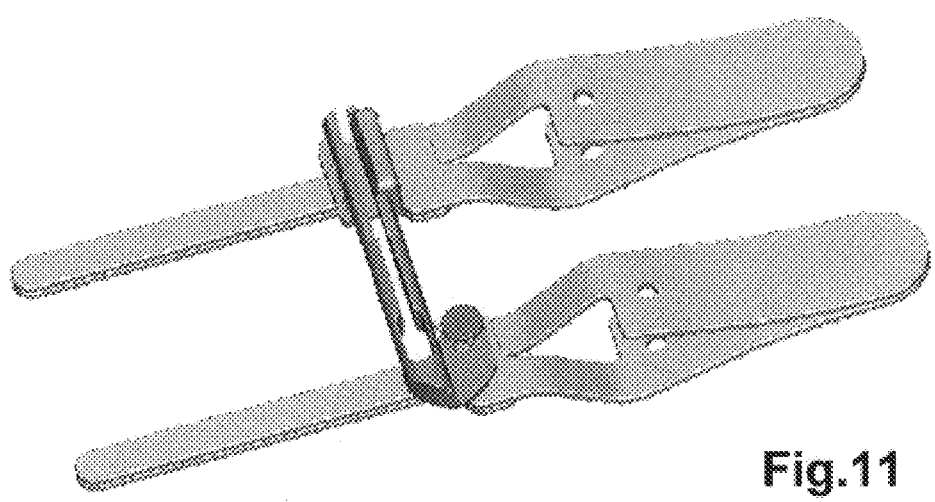

The second clamp 21, shown in FIGS. 7–9, has a lock/release control 22 that receives and locks the connecting arm 12 of the first clamp, and allows adjustment of the distance between the two clamps at various lengths. The lock/release control 22 has a flattened cylindrical bore 23, with arcuate surfaces 24 on the sides of the bore and flattened planar surfaces 26 (best seen in FIG. 8) on the top and bottom, which cooperates with the connecting arm 12 on the first clamp to hold the clamps in the properly aligned position. As shown in FIGS. 3–6, the connecting arm 12 on the first clamp in comprises a slender "U", with prongs 28 in the shape of flattened semi-cylindrical sections. There is a short cylindrical bore 32 at each side of the flattened central bore 23 (FIG. 9) to facilitate connection of the clamps. The tips of the prongs 28 can be inserted into the cylindrical bores 32 without regard to the angular relationship of the two clamps. One or both clamps can then be rotated to bring the flattened edges of prongs 28 into alignment with the flattened sections in the central bore 23 of lock/release control 22, to allow the prongs of connecting arm 12 to be fully inserted into the lock/release control, and to align the individual clamps 11, 21 as shown in FIGS. 1 and 2, with the individual clamps 11, 21 besides each other, substantially in the same plane and substantially parallel.

Figure 12:
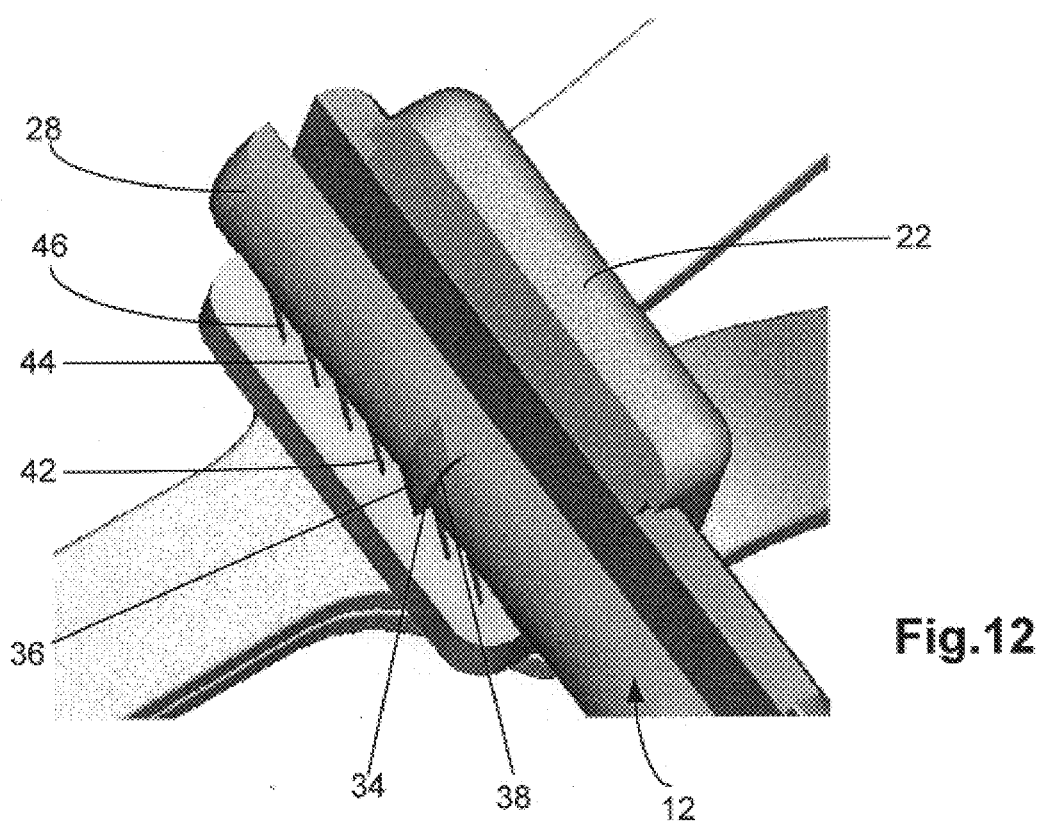

As is perhaps best shown in FIGS. 6 and 12, the connecting arm has one or more rings or teeth 34 with sloping front surfaces 36 (the first surfaces to enter the lock/release control) and rear surfaces 38 which extend at substantially right angles to the axis of the connecting arm. The lock/release control on the second clamp has a series of complementary rings or teeth 42 that are engaged by the teeth on the connecting arm.

Figure 3:
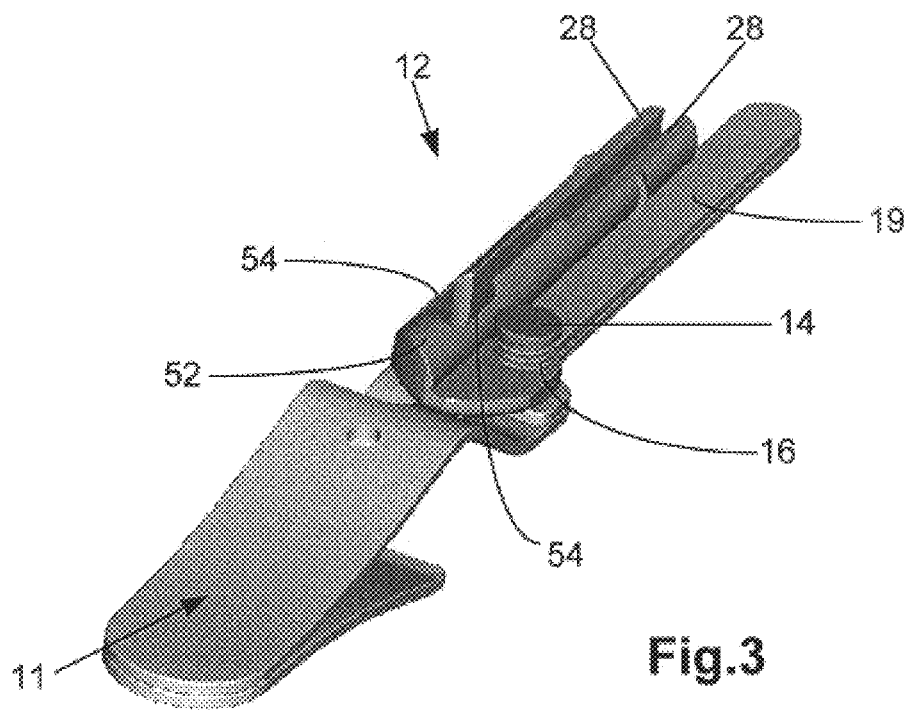
FIGS. 3–6 are perspective views of the clamp that bears the connecting arm.
Figure 4:
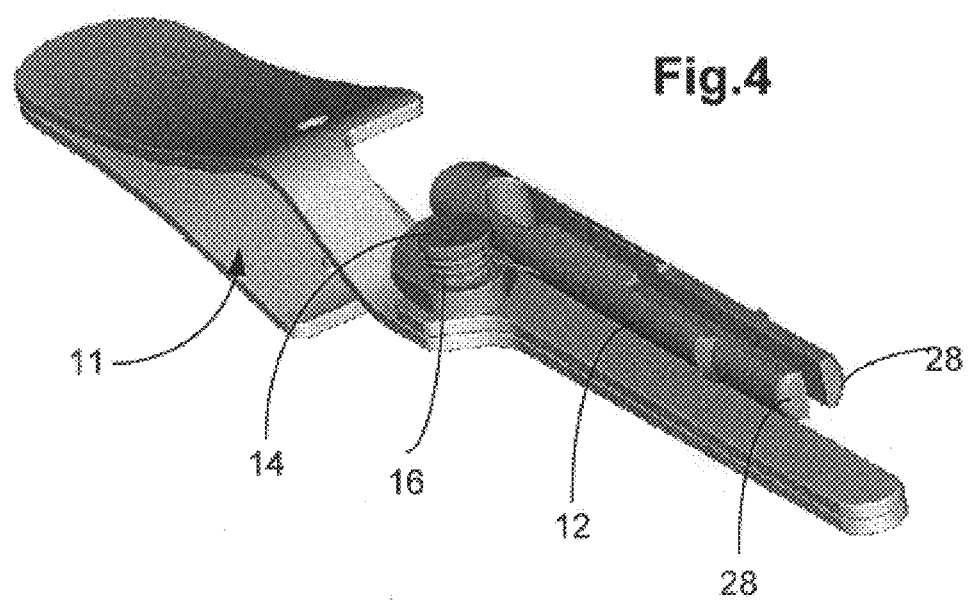
Figure 5:
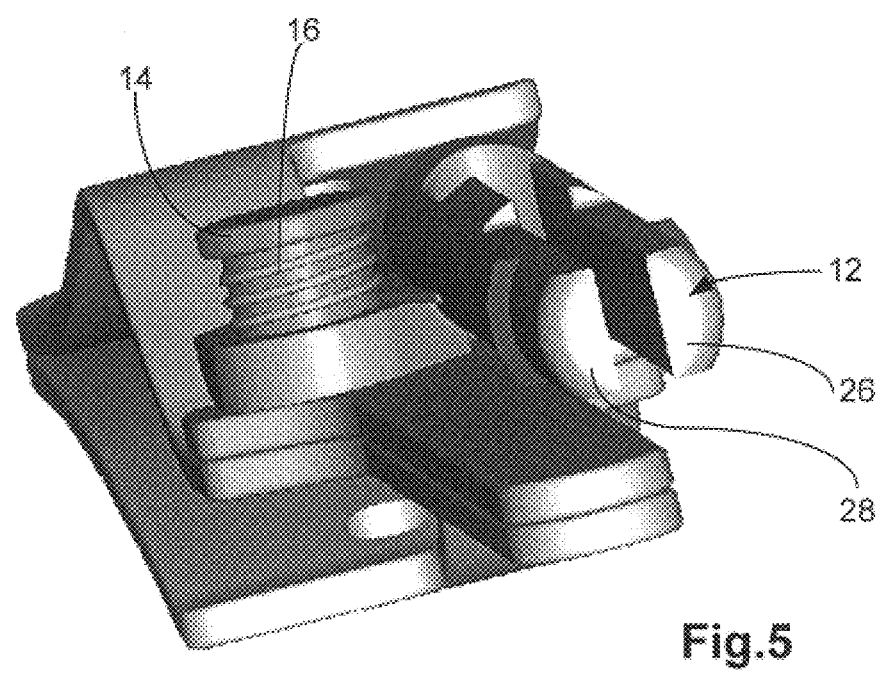

As shown in FIGS. 3 and 4, the prongs 28 of the connecting arm are joined to a base 52, mounted on pivot 14, by relatively thin sections or webs 54. These webs allow the prongs 28 to flex as they are inserted into the lock/release control. This lets the sloping front surfaces 36 of the teeth on the arms ride over the complementary sloping surfaces 44 of the teeth 42 in the lock/release control. The rear surfaces 38, 46 of teeth 34 and 42 lock connecting arms 42 in place until prongs 28 are manually depressed. When the prongs are depressed, they can be withdrawn from the lock/release control 21. The distance between the clamps, and blood vessels or other tissue held therein, can be adjusted by inserting the connecting arms further into the lock/release control, or by partially withdrawing the arms.

Other sets of paired clamps embodying this invention may be connected by other means, including friction and other mechanical connectors and non-mechanical connectors such as magnetic couplings. In yet another embodiment, both clamps may be mounted on a pivoting connecting arm that permits the clamps and arm to be aligned for insertion through the trocar. This version may be preferable in procedures where the vessels to be anastomosed are already adequately aligned, i.e. approximately in a straight line and relatively close together, because it eliminates the need to connect the two clamps together intracorporeally. However, when the vessel ends are not in a straight line or are retracted significantly, the separable clamps shown in the FIGURES of this application will normally be preferable.

Figure 15:
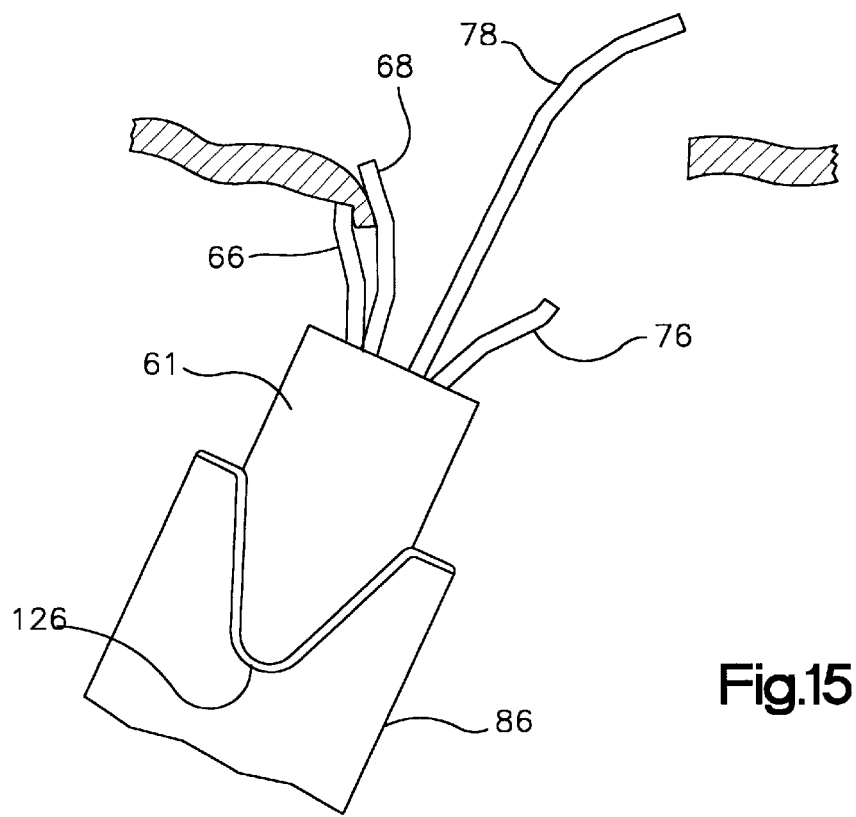
FIGS. 15–18 are enlarged fragmentary views of the tip of the approximator-everter in FIGS. 13 and 14, sequentially illustrating the steps in the capture, eversion and approximation of the edges of two vessels.
Figure 16:
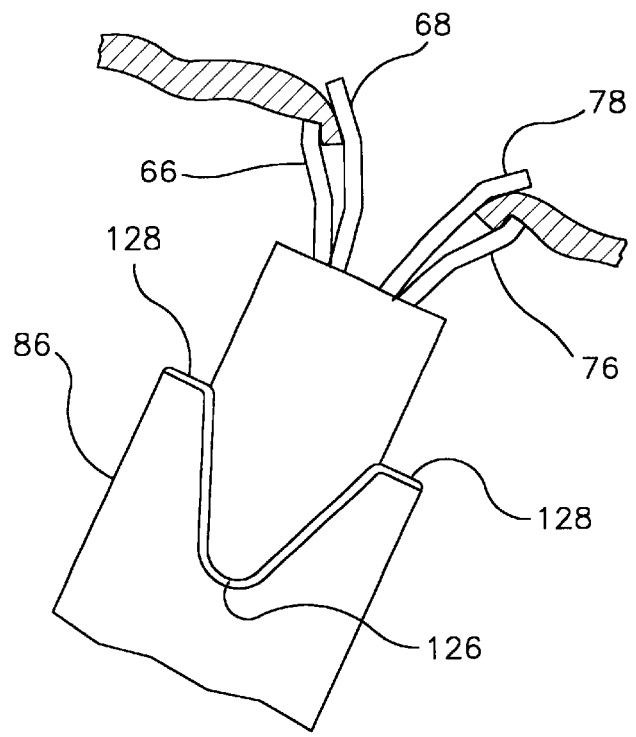

The approximator-everter shown in FIGS. 13–18, referred to generally as 60, is designed to allow final approximation and eversion of blood vessel edges (thereby eversion and approximation of their intimal layers) in preparation for anastomosis, preferably by laparoscopic vascular clip application and alternately by sutures, adhesives or other surgical fasteners. Approximator-everter 60 is equipped with a pair of vessel edge grippers 64, 74, each composed of two flat nontraumatic blades 66, 68, 76, 78 which secure the two edges of the vessels, housed in a support or core tube 61. The angle, width, shape and surface of the blade tips, and the relative angles of the inner blades 68, 78 and outer blades 66, 76 of the grippers may be varied to suit the tissue to be gripped. For example, the tips of the outer or stationary blades 66, 76 may be curved as shown in FIG. 15, or one or both blades of each gripper may be provided with grooves, teeth, roughened surfaces, adhesive or other means to better grip and secure the tissue to be everted.

The two edge grippers 64, 74 can be controlled and applied independently of each other so that the approximator-everter can be used to capture the edge of one blood vessel, or other tissue, and then used to capture another vessel or other tissue to bring the two together. The blades of each gripper can also be operated independently. For example, the outer blade of each gripper may be welded or otherwise secured to the inner tube of the everter. The edges of a blood vessel, or other tissue, can then be gripped by retracting one of the inner blades, or by advancing the inner blade as shown in FIG. 15, and allowing it to retract to the position shown in FIG. 16 under the influence of a spring or other biasing means. Biased return is preferred because it provides somewhat greater control over the force exerted on the tissue by the grippers.

The blades of the grippers may be operated with various actuating mechanisms, including the one shown in FIGS. 19a, 19b, 20 and 21 and the one shown in FIGS. 22 and 23. The actuating mechanism illustrated in FIGS. 19a, 19b, 20 and 21, referred to generally as 80, has an upper handle 82 (shown in FIGS. 20 and 21 and a pivoted lower handle 84 that can be squeezed toward the upper handle, as illustrated in FIG. 19b, to advance sheath 86 around the blades 66, 68, 76, 78 of the grippers 64, 74. A frame 92, mounted within upper handle 82, as shown in FIGS. 20 and 21, holds independently controlled slides 94, 96 for advancing and retracting the moveable inner blades 68, 78 of the grippers. The fixed outer blades 66, 76 are attached to frame 92 with lock down screws 98, one of which is shown in FIG. 20. The movable inner blades 68, 78 are attached, by screws 102, 104, to bosses 106, 108 that extend laterally from slides 94, 96. Coil springs 112, one of which is shown in FIG. 20, bias the slides 94, 96 and the moveable inner gripper blades 68, 78 to the closed position shown in FIG. 20. The biasing force, and the pressure exerted on tissue by the grippers can be adjusted with bolts 114, threaded into bores 116 that house the springs 112, or by varying the spring thickness or spring rate.

Figure 17:
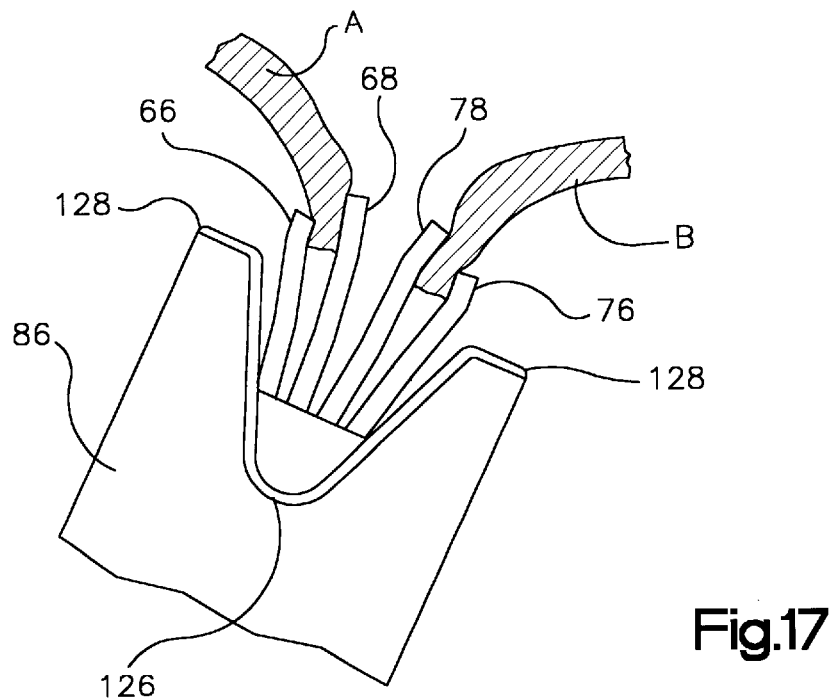
Figure 18:
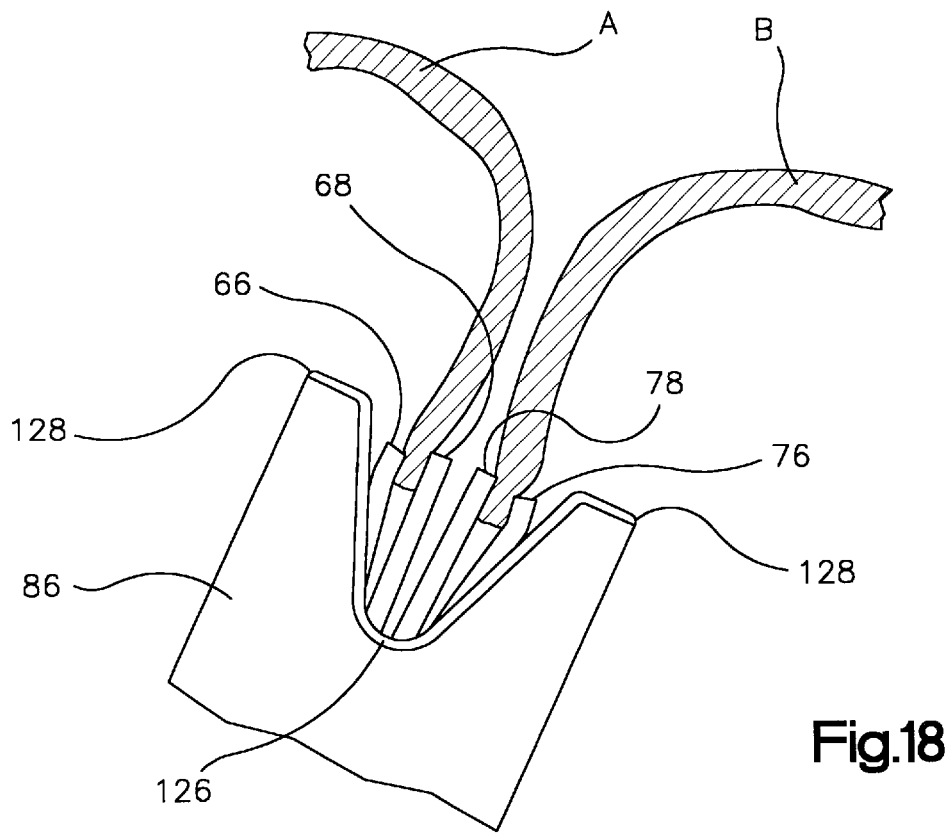

The grippers 64, 74 are opened to secure tissue by pressing buttons 118 (extending upwardly from slides 94, 96) forward to advance the slides and the moveable inner blades 68, 78 to the advanced position shown in FIG. 20. When both vessel edges have been secured (one in each gripper) the everter sheath 86 is advanced by squeezing lower handle 84, as shown in FIG. 19b. The lower handle is connected to sheath 86 by a pivoted link 122, one end of which is attached to the upper handle 82, and a connecting rod 124. When the lower handle 84 is squeezed toward the fixed upper handle 82, the pivoted link 122 advances the connecting rod 124 and the sheath 86 advances to surround the blades of grippers 64 and 74. The distal or outer end of sheath 86 has two notches 126 on opposite sides of the sheath. When the outer sheath 86 is fully advanced or extended, as shown in FIG. 18, the tips 128 of the sheath press against the fixed outer blades 66 and 76, and the vessel edges A and B held by grippers 64, 74 are pulled into the notches 126, as shown in FIGS. 17 and 18. In the process edges A and B automatically everted to produce intima-intima approximation. Vascular clips, sutures, adhesives or other surgical fasteners can then be inserted or applied, adjacent to the gripper, in vessel edges A and B, which extending beyond the notches 126 at a substantially right angle to the plane of FIG. 18. The vessel edges are released by allowing the sheath to retract, and advancing the inner blades to open the grippers.

In the actuator illustrated in FIGS. 22 and 23, referred to generally as 130, the support or core tube that houses the blades 66, 68, 76, 78 of grippers 64 and 74 is mounted in a "pistol grip" handle 132. The moveable inner blades 66, 76 of the grippers, which are normally in the open position with this actuator 130, can be retracted individually by squeezing trigger 134. The retracted blades are held in the retracted position by a locking mechanism (not shown) in handle 132, and a "T" handle advances the sheath 86 to evert and approximate tissue held by the grippers 64 and 74. The blades are released upon completion of anastomosis by pressing a button to release the locking mechanism.

Use of the instruments embodying this invention on a synthetic vessel is illustrated schematically in FIGS. 24 and 25. Each vessel end is secured by a bulldog clamp introduced through the trocar. The two bulldog clamps, preferably paired clamps as illustrated in FIGS. 1–12, can be assembled laparoscopically, followed by adjustment of the distance between the two vessel ends to achieve optimal working distance, as shown in FIG. 24. The two vessel edges can be approximated and everted using the novel vessel edge approximator-everter, after which VCS clips or sutures can be applied as shown in FIG. 25. After completion of half of the circumference of the anastomotic site, the paired bulldog clamps with the vessel ends are turned over (180 degrees) to complete the second half of the anastomosis. After circumferential clip approximation at the anastomotic site, the two clamps are detached from the vessel and then disassembled. The clamps are then extracted through the trocar.

The laparoscopic vascular forceps illustrated in FIGS. 23–27 are designed for manipulating and securing delicate body tissues, especially blood vessel edges, in an atraumatic manner in the laparoscopic setting. The proposed device can facilitate suturing, clipping, and other laparoscopic reconstructive maneuvers, such as the vascular procedures described herein and in the publications and patents listed above. Unique design features include the tip (distal end) of the device, which consists of two gripping jaws, each angulated at its mid/distal portion and tapered at the most distal end. The atraumatic tips are fine and tapered, which allows fine, manipulative surgical maneuvers without tissue damage. The jaws can open and close to allow delicate, atraumatic handling of the tissues. Each jaw may be equipped with grooves on the inner surface of the jaws (tissue contact surface) that may provide better gripping/ securing of tissues. The body of each jaw may be angulated (from 0–60°), and the jaws may rotate as a unit, to allow easier application of the device from different surgical access sites/positions. As best seen in FIG. 27, the forceps are preferably provided with inner or secondary jaws that are adapted to grip a surgical needle. Thus, these forceps can be used for either holding or manipulating blood vessel edges or other tissue, or securing or manipulating a needle, which further increases their flexibility and adaptability.

Those skilled in laparoscopic surgery will readily understand from the foregoing description that this invention provides instruments and procedures that dramatically facilitate the handling, approximation, eversion and anastomosis of vascular and other tissue. This removes one of the major obstacles to the development of laparoscopic vascular surgery. This in turn promises to reduce post operative morbidity, recovery periods, hospital stays and health care costs, and provide better cosmetic results. Of course, those skilled in laparoscopic surgery will also recognize that many modifications may be made in the instruments and procedures described herein. These embodiments are merely illustrative of many instruments and procedures within the scope of this invention, which is defined by the following claims.

We claim:

1. A surgical instrument comprising a first clamp and a second clamp adapted to be inserted through a trocar or other port into a surgical field and then positioned on a support so that said first clamp and said second clamp hold and position one or more vessels or elongated tissues, wherein:

said support comprises a connecting arm mounted on said first clamp and a mount for securing said second clamp on said connecting arm; and said connecting arm is pivotally mounted and spring loaded on said first clamp so that said connecting arm-can pivot to extend axially along said first clamp when said clamp passes through said trocar or other port, and said first clamp automatically pivots into a position substantially perpendicular to said connecting arm when the clamp has passed through the port.

2. A surgical instrument according to claim 1 wherein said first clamp and said second clamp are positioned on said support with said first clamp so that jaws of said first clamp and jaws said second clamp are positioned to grip the ends of two vessels, or two elongated tissues, that are substantially aligned with each other.

3. A surgical instrument according to claim 1 wherein said first clamp and said second clamp are positioned on said support with said first clamp beside, in the same plane as and substantially parallel to said second clamp.

4. A surgical instrument according to claim 1 wherein said mount is adapted to releasably lock said second clamp on said connecting arm.

5. A surgical instrument comprising a first clamp and a second clamp adapted to be inserted through a trocar or other port into a surgical field and then positioned on a support so that said first clamp and said second clamp hold and position one or more vessels or elongated tissues, wherein:

said support comprises a connecting arm mounted on said first clamp and a mount for securing said second clamp on said connecting arm; and said mount comprises one or more locking rings or teeth and said connecting arm comprises a pair of substantially parallel webs with said one or more locking rings or teeth on the outsides of said webs, said teeth on the webs being adapted to engage the teeth on the mounts and lock said second clamp on said connecting arm, and said webs being adapted to flex to release said second clamp from said arm.

6. A surgical instrument according to claim 5 wherein said mount comprises a series of locking rings or teeth that provide adjustment of the distance between first clamp and the second clamp by inserting the connecting arm further into the the distance between the mount or partially withdrawing the connecting arm from the mount.

7. A surgical instrument comprising a first clamp and a second clamp adapted to be inserted through a trocar or other port into a surgical field and then positioned on a support so that said first clamp and said second clamp hold and position one or more vessels or elongated tissues, wherein:

said support comprises a connecting arm mounted on said first clamp and a mount for securing said second clamp on said connecting arm; and said connecting arm has a partially cylindrical cross-section, with one or more flat spots on the sides of said arm, and said mount has a flattened cylindrical cross-section that complements the cross-section of said arm and positions the second clamp on said connecting arm in a desired angular relation with respect to said first clamp.

8. A surgical instrument comprising a first clamp and a second clamp adapted to be inserted through a trocar or other port into a surgical field and then positioned on a support so that said first clamp and said second clamp hold and position one or more vessels or elongated tissues, wherein:

said support comprises a connecting arm mounted on said first clamp and a mount for securing said second clamp on said connecting arm; and said first clamp and said second clamp are pivotally mounted and spring loaded on a pivoting connecting arm so that said first clamp and said second clamp may be pivoted to extend generally axially along said connecting arm for insertion and removal of the instrument through a trocar or other port into a surgical field and automatically pivot into a position substantially perpendicular to said connecting arm when the clamp has passed through the port.

9. A surgical instrument comprising a first clamp and a second clamp adapted to be inserted through a trocar or other port into a surgical field and then positioned on a support so that said first clamp and said second clamp hold and position one or more vessels or elongated tissues, wherein said first clamp is attached to said second clamp with a magnetic coupler.

10. An instrument for laparoscopic vascular surgery comprising a first clamp and a second clamp adapted to be inserted through a trocar or other port into a surgical field and then positioned on a support so that said first clamp and said second clamp approximate the ends of a first end of a blood vessel and a second end of a blood vessel for anastomosis;

a connecting arm mounted on said first clamp so that connecting arm can pivot to extend axially along said first clamp when said first clamp passes through said trocar or other port and can pivot into a position transverse to said connecting arm when the first clamp has passed through the port, said connecting arm being biased towards said transverse position; and said second clamp comprises a mount adapted to releasably lock said second clamp on said connecting arm.

11. An apparatus for surgical manipulation of tissue comprising:

a support;

a first set of blades mounted on said support, with at least one of said blades being mounted for reciprocating movement with respect to said support;

a second set of blades mounted on said support, with at least one of said second set of blades being mounted for reciprocating movement with respect to said support;

a sheath mounted on said support and adapted to surround said first set of blades and said second set of blades, said sheath having notches in opposing sides of the sheath, said notches being designed and adapted to receive tissue gripped by said blades when said blades are surrounded by said sheath;

means for extending and retracting at least one blade in said first set of blades to grip tissue between the blades of said first set, means for extending and retracting at least one blade in said second set of blades to grip tissue between the blades of said second set, and means for bringing said first set of blades and said second set of blades within said sheath to bring the tissue gripped by said first set of blades and the tissue gripped by said second set of blades into the notches in the sides of the sheath, whereby said tissue is everted to approximate the intimal layer of the tissue gripped by said first set of blades and the intimal layer of the tissue gripped by said second set of blades.

12. The apparatus for surgical manipulation of tissue according to claim 11 wherein said sheath is adapted for reciprocating motion with respect to said support, whereby said sheath may be extended to bring said first set of blades and said second set of blades within said sheath.

13. The apparatus for surgical manipulation of tissue according to claim 11 wherein at least one blade in said first set of blades and at least one blade in said second set of blades are secured to said support.

14. The apparatus for surgical manipulation of tissue according to claim 11 wherein tips of one or more of said blades are provided with grooves, teeth, roughened surfaces, adhesive or other means for improved gripping of tissue.

* * * * *